United States Patent [19]

Lee

[11] Patent Number: 5,477,157
[45] Date of Patent: Dec. 19, 1995

[54] METHOD AND APPARATUS FOR DETECTING FLAWS OF A SEAM IN A SHIELDED ENCLOSURE

[75] Inventor: Youn Lee, Clifton, Va.

[73] Assignee: The United States of America as represented by the Secretary of the Army, Washington, D.C.

[21] Appl. No.: 283,861

[22] Filed: Aug. 1, 1994

[51] Int. Cl.6 ................................. G01R 27/26
[52] U.S. Cl. ........................ 324/718; 174/35 MS
[58] Field of Search ......................... 324/627, 718, 324/715, 713, 525, 127; 174/35 MS

[56] References Cited

U.S. PATENT DOCUMENTS

| | | | |
|---|---|---|---|
| 3,599,095 | 8/1971 | Johnson | 324/64 |
| 3,611,125 | 10/1971 | Sharon et al. | 324/627 |
| 3,995,213 | 11/1976 | Robinson et al. | 324/627 |
| 4,789,829 | 12/1988 | Stribling | 324/627 |
| 4,888,546 | 12/1989 | Berry et al. | 324/715 |
| 5,061,899 | 10/1991 | Kudo | 324/627 |
| 5,153,524 | 10/1992 | McCormack | 324/627 |

OTHER PUBLICATIONS

"A New Apparatus for Detecting Flaws of a Seam in a Shielded Enclosure", by Lee, IEEE 1993 International Symposium on Electromagnetic Compatability, Aug. 9–13, Dallas, Texas.
IBM Technical Disclosure Bulletin vol. 17, No. 7, Dec. 1974 Anderson et al. Portable Resistance Gage.
IEEE Transactions vol. EMC12, No. 1 Feb. 1970 Jarva Shielding Tests for Cables and Small Enclosures.

*Primary Examiner*—Maura K. Regan
*Attorney, Agent, or Firm*—Freda L. Krosnick; Frank J. Dynda

[57] ABSTRACT

Flaws in a seam of a shielded enclosure are detected by forcing a current to flow over the shielded enclosure and the seam. A small portable, hand held, compact device is placed over the seam. The device has a high impedance path which forces current to flow over the shielded enclosure and the seam. Two electrodes are resiliently pressed towards the shielded enclosure. The current flowing across the seam produces a voltage which the first and second electrodes and a detector use to detect flaws in the seam.

26 Claims, 8 Drawing Sheets

METHOD AND APPARATUS FOR DETECTING FLAWS OF A SEAM IN A SHIELDED ENCLOSURE

TECHNICAL FIELD

This invention is in the field of detection of flaws in a seam formed by metallic sheets and rivets, gaskets, or welding in a shielded enclosure used to protect against unwanted electromagnetic interference or radio frequency interference fields.

BACKGROUND ART

Conventional techniques for detecting flaws in a seam of a shielded enclosure involve measuring shielding effectiveness by using an antenna to illuminate a seam and its vicinity under test, and also using a probe or an antenna to detect the leaked energy at the opposite side. Several widely accepted standards that use this type of technique are MIL-STD-285, NSA-65-6, IEEE-STD-299-1991, MIL-STD-188-125, and MIL-STD-907B. There are major deficiencies associated with this measurement technique in that all seams and walls have to be accessible from both sides for testing. Due to this shortcoming, inaccessible areas are largely ignored or exempt from testing. In addition, the receiving antenna not only captures the field leaked through the

SUMMARY OF THE INVENTION

These and other disadvantages of the prior art have been overcome by the apparatus and method of the present invention. Flaws in a seam of a shielded enclosure are detected by forcing a current to flow over the shielded enclosure and seam by placing a hollow metallic device, including first and second electrodes, a high impedance path and an opening, so that the opening encloses the seam. The device is electrically coupled to a continuous wave signal source. The first and second electrodes are resiliently pressed towards the shielded enclosure so that the seam is positioned between the first electrode and the second electrode. The current flowing across the seam, between the first and second electrodes, produces a voltage which is measured to detect flaws in the seam. The high impedance path in the device forces current to flow over the shielded enclosure and the seam. The high impedance path includes a thin dielectric material with a high dielectric constant. The thin dielectric material is positioned in a gap in the hollow metallic device. The high impedance path also includes a first metallic extrusion and a second metallic extrusion. The thin dielectric material is positioned between the first and second metallic extrusions. The thin dielectric material is positioned in parallel with the seam. The hollow metallic device is rectangular in shape.

The first electrode is positioned at a first level and the second electrode is positioned at a second level which is different from the first level. The current flowing across the seam produces a voltage across the seam. The voltage is measured by a spectrum analyzer. A thin dielectric sheet is positioned between the hollow metallic device and the shielded enclosure. A transfer seam impedance is measured.

A hand held apparatus for detecting flaws in a seam of a shielded enclosure by forcing a current to flow over the shielded enclosure and the seam in accordance with the present invention includes a hollow metallic device, with a high impedance path and an opening positioned over the seam so that the opening encloses the seam, a first electrode and a second electrode, which are mechanically coupled to the device, a first spring which resiliently presses the first electrode towards the shielded enclosure, a second spring which resiliently presses the second electrode towards the shielded enclosure, so that the seam is positioned between the first electrode and the second electrode. As noted above, the high impedance path forces current to flow over the shielded enclosure and the seam. The high impedance path includes a thin dielectric material with a high dielectric constant. The thin dielectric material is positioned in a gap in the hollow metallic device. The high impedance path further includes a first metallic extrusion and a second metallic extrusion so that the thin dielectric material is positioned between the first and second metallic extrusions. The thin dielectric material is positioned in parallel with the seam. The hollow metallic probe is rectangular in shape. The first electrode is positioned at a first level and the second electrode is positioned at a second level which is different from the first level. A thin dielectric sheet is positioned between the hollow metallic probe and the shielded enclosure.

A hand held apparatus, for detecting flaws in a seam of a shield enclosure by forcing a current to flow over the shield enclosure and the seam, in accordance with the present invention includes a first metal bracket including a first connector and a first extrusion, a second metal bracket including a second connector and a second extrusion, a thin dielectric material sandwiched between the first and second extrusions so that the first and second brackets form a hollow metallic device with an opening, two insulated wires each connecting the first connector and the second connector, the two insulated wires forming an oval shape, a first electrode mechanically coupled to the first metal bracket and resiliently pressed towards the shielded enclosure, and a second electrode mechanically coupled to the second metal bracket and resiliently pressed toward the shielded enclosure. The opening is positioned over the seam so that the seam is between the first electrode and the second electrode. The first and second connectors are coaxial connectors. The first connector is electrically coupled to a continuous-wave signal source. The second connector is coupled to a termination resistor. The high impedance path forces current to flow over the shielded enclosure and the seam. The thin dielectric material is positioned in parallel with the seam. The hollow metallic device is rectangular in shape. A further embodiment positions the first and second metal brackets at a right angle for measuring corners.

An apparatus for detecting flaws in a seam of a shielded enclosure includes a signal source, a hand held device, including a first connector and a second connector, two insulated wires each connecting the first connector and the second connector, said two insulated wires forming an oval shape, a first metal bracket with a first extrusion, a second metal bracket with a second extrusion, a thin dielectric material coupled to the first and second extrusions, a first electrode mechanically coupled to the first metal bracket, a second electrode mechanically coupled to the second bracket, a termination resistor coupled to the second connector, and a detector coupled to the first and second electrodes.

The above and other features of the invention, including various novel details of construction and combinations of parts, will now be particularly described with reference to the accompanying drawings and pointed out in the claims. It will be understood that the particular device embodying the invention is shown by way of illustration only and not as a limitation of the invention. The principles and features of this invention will be employed in various and numerous

DETAILED DESCRIPTION OF THE INVENTION

Figure 1:
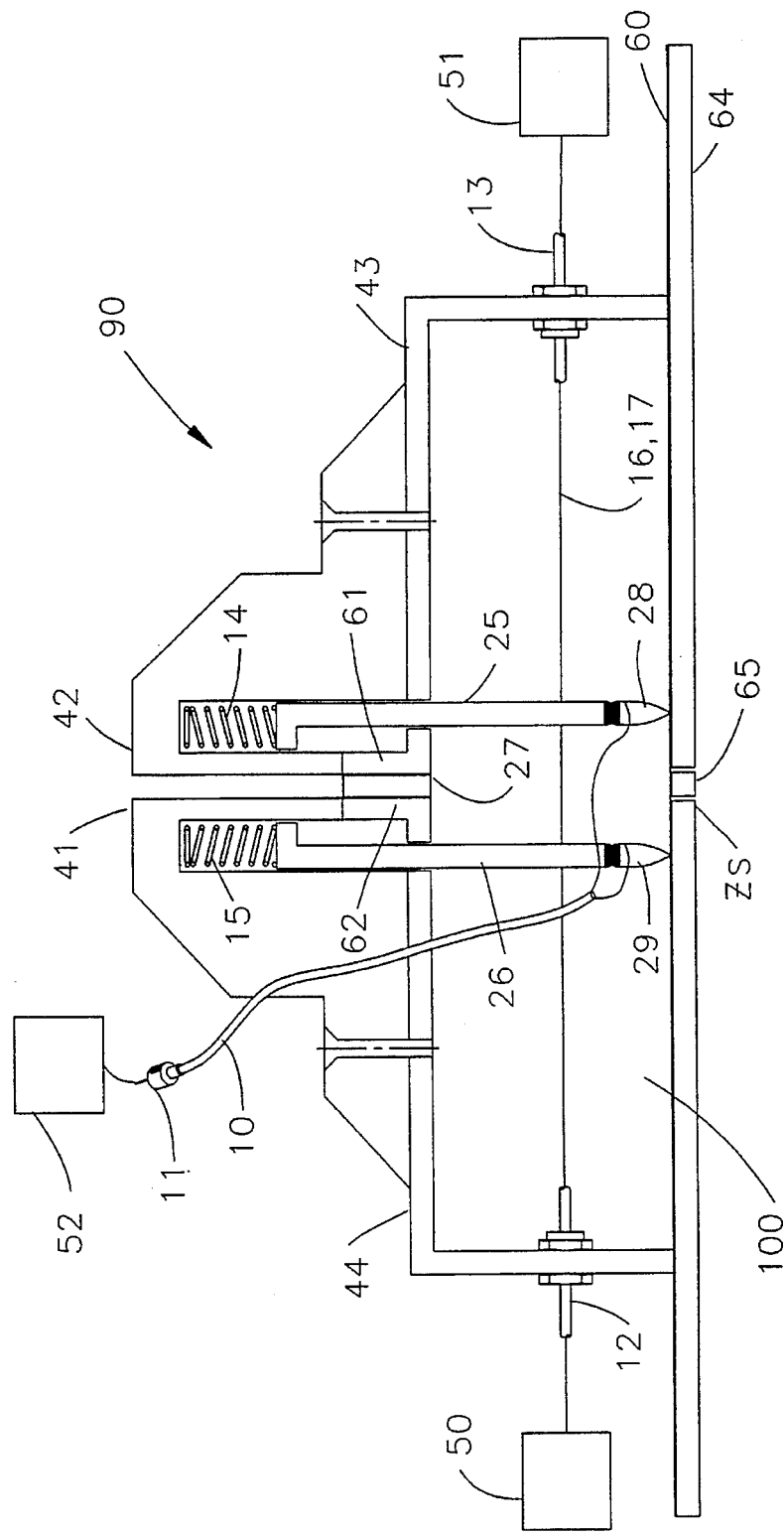
FIG. 1 is a center-cut side view of the hand held apparatus of the present invention designed to be used on a flat or bilevel surface.

Now turning to the preferred embodiment, FIG. 1 illustrates a hand held apparatus 90 for detecting flaws of a seam in a shielded enclosure in accordance with the present invention. A first bracket 44 and a second bracket 43 are made of highly conductive metal and are joined to form a hollow metallic device with an opening 100. The first extrusion 62, which is part of the first bracket, and second extrusion 61, which is part of the second bracket, are located at the center of the apparatus. The extrusions minimize radiation occurring at the center of the apparatus when it is placed on a bilevel surface. The first coaxial connector 12 is mechanically coupled to the first bracket 44. Signal source 50 is electrically coupled to coaxial connector 12. Coaxial connector 13 is mechanically coupled to second bracket 43, and electrically coupled to termination resistor 51. Two insulated wires, 16 and 17, are connected to the center conductors of coaxial connectors 12 and 13, and form an oval shape.

Figure 4:
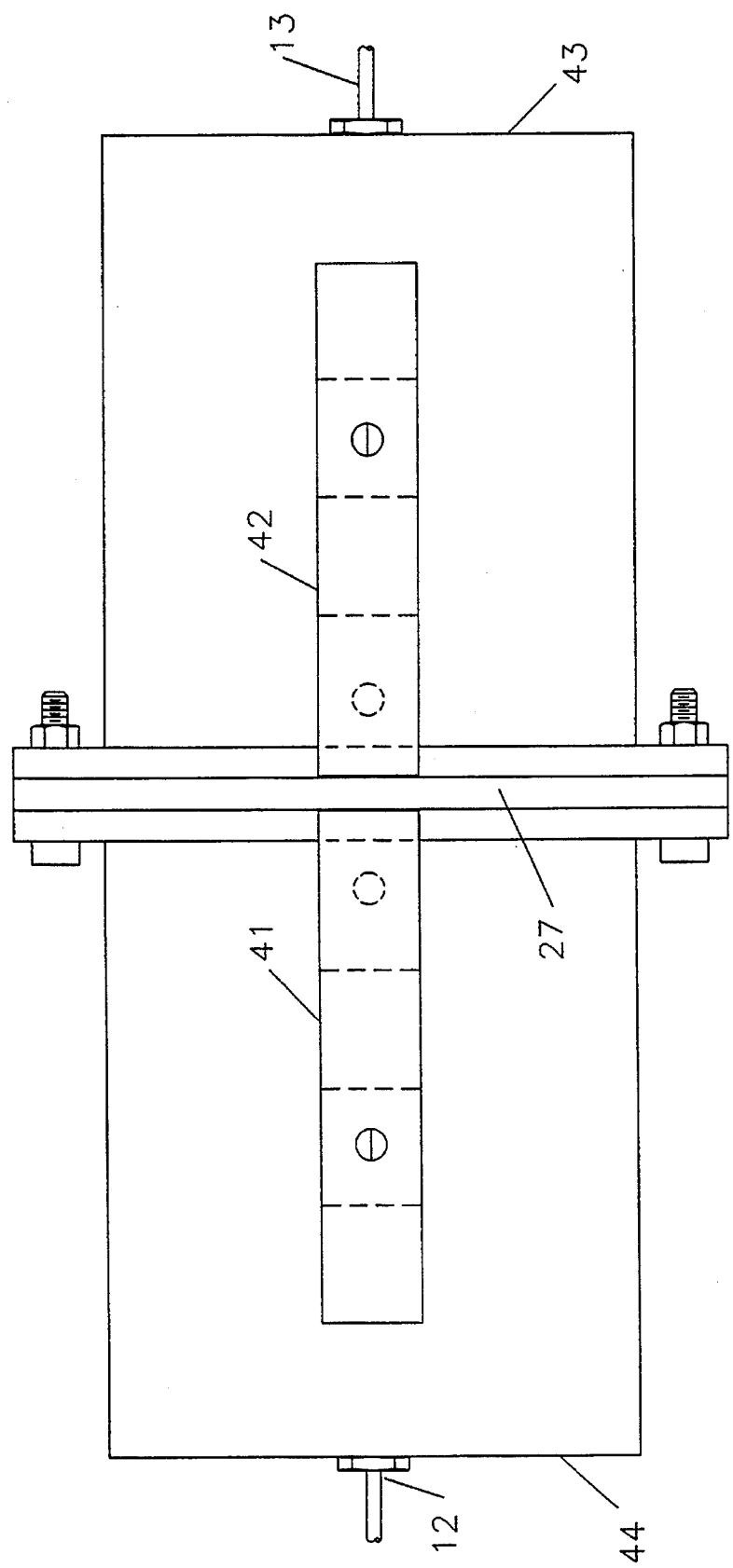
FIG. 4 illustrates a top view of the hand held apparatus of the present invention.
Figure 5:
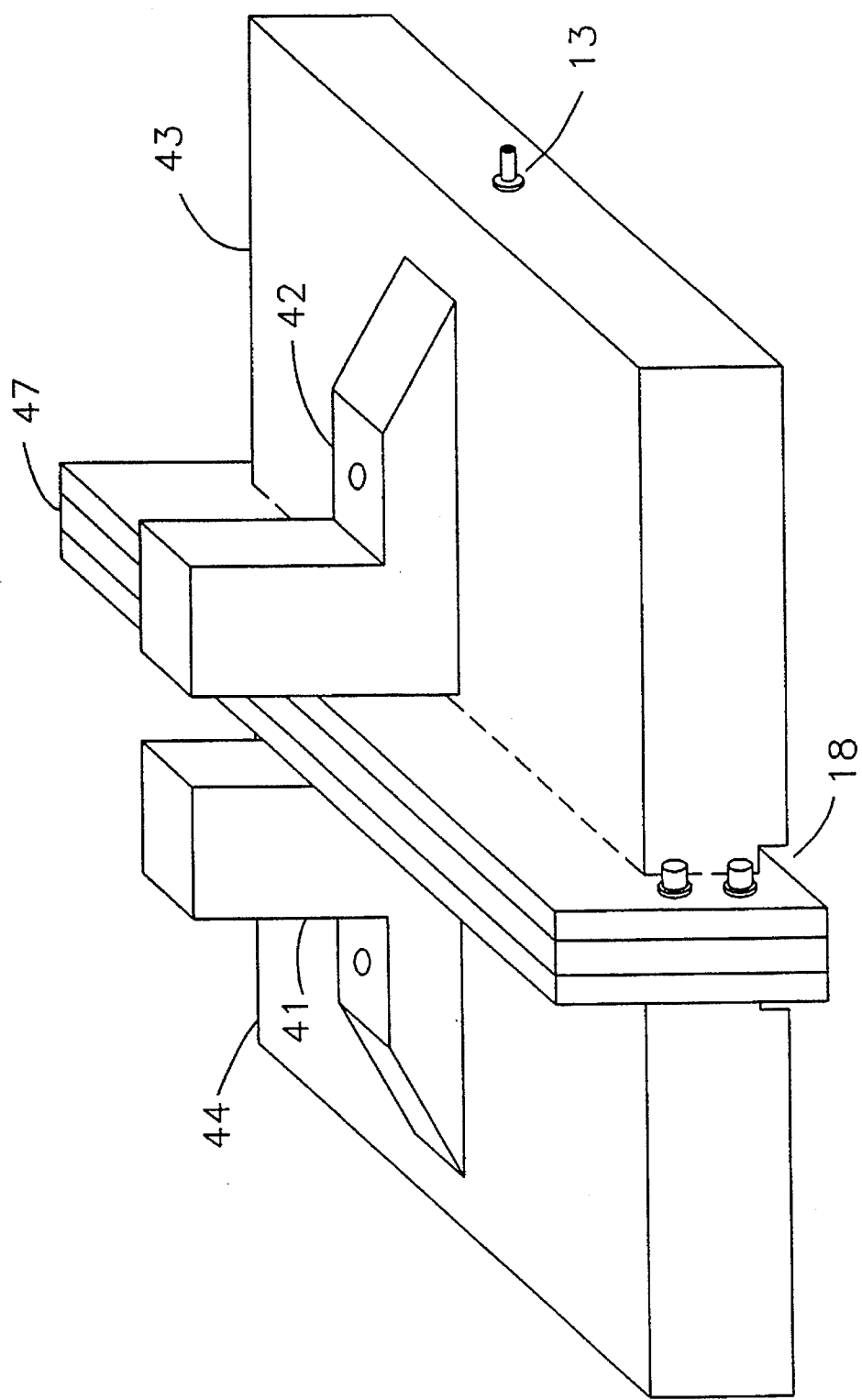
FIG. 5 is a schematic drawing of the apparatus of the present invention.

Electrodes 28 and 29 are mounted on the bottom of dielectric rods 25 and 26, and springs 14 and 15 push the dielectric rods downward. Elements 41 and 42 can be made of either metal or dielectric material and hold springs 14 and 15 and dielectric rods 25 and 26 in place. Dielectric rods 25 and 26 move up and down in elements 41 and 42, respectively, with little friction or rotation. Grease can be applied to the dielectric rod channels to reduce friction if necessary. As shown in FIG. 4, elements 41 and 42 are secured to the top center portion of brackets 43 and 44 using screws and by abutting against the extrusion.

A very thin dielectric material 27 having a relative high dielectric constant electrically separates the first and second brackets 43 and 44. The thin dielectric material 27 can be bonded to brackets 43 and 44 using an adhesive. Only one dielectric material 27 is necessary to insulate items 43 and 44, but it is convenient to apply very thin dielectric materials on each end of items 43 and 44 for bilevel application.

One end of the twisted wire pair 10 is soldered to electrodes 28 and 29, and the other end is connected to a coaxial connector 11. For frequencies above 1 megahertz, the twisted wire pair 10 should be shielded properly to eliminate interference.

Figure 2:
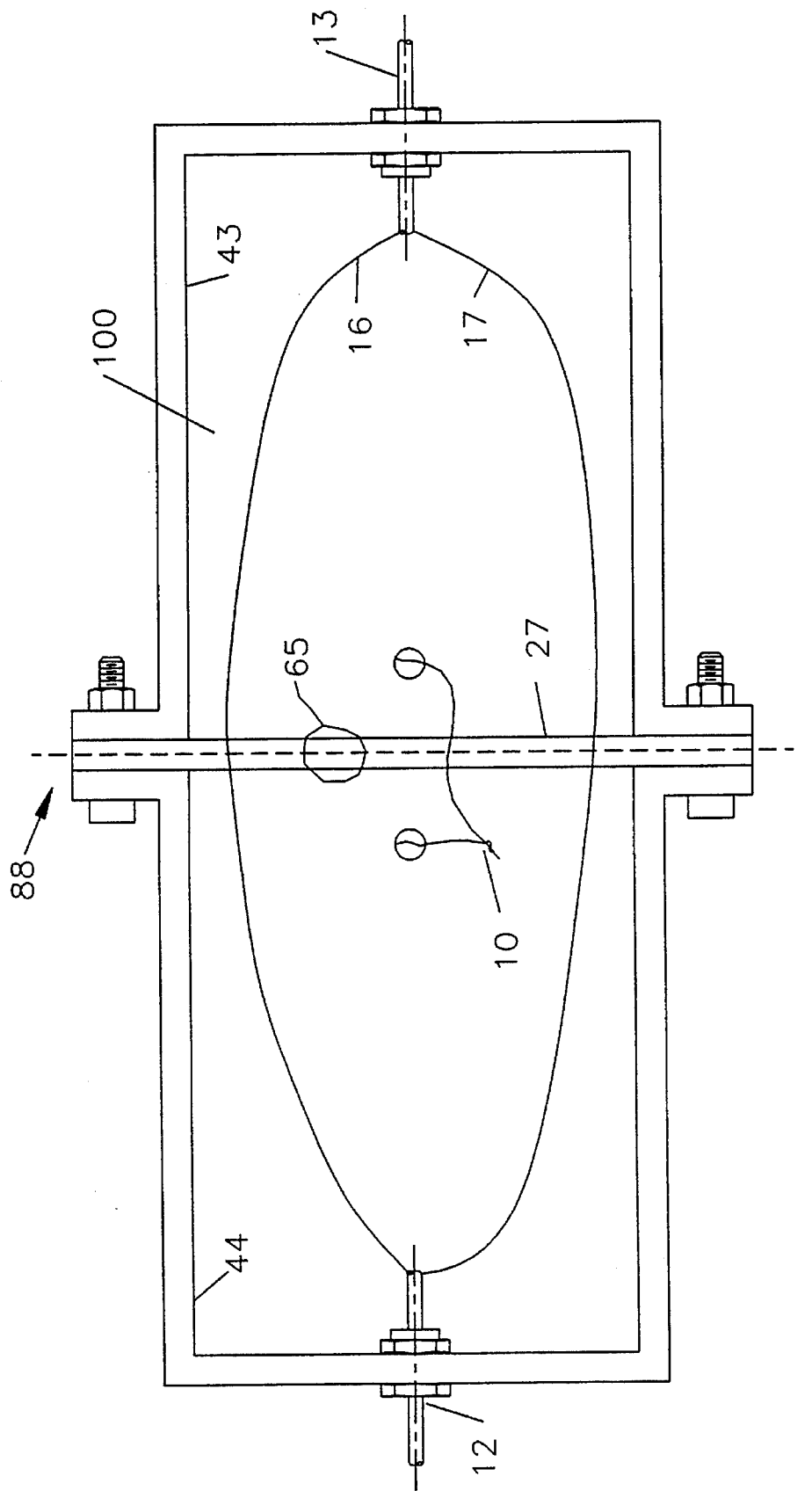
FIG. 2 illustrates a bottom view of the hand held apparatus of the present invention.

FIG. 2 illustrates the bottom view of the apparatus, showing the oval shaped routing of insulated wires 16 and 17. The two wires 16 and 17 are connected to the center conductors of coaxial connectors 12 and 13.

In operation, the high impedance path in the apparatus formed by the first and second brackets 44 and 43, forces the currents generated by signal source 50 to flow through the shielded enclosure section 64, and the seam 88 with gasket 65. Because of the use of resilient pressing or springs to move electrodes 28 and 29, the apparatus of the present invention can easily accommodate bilevel surfaces.

To test a seam 88 with a gasket 65, the apparatus is placed over the seam so that the thin dielectric material 27 is parallel with and just above the seam. Extrusions 61 and 62 on brackets 43 and 44, the dielectric material 27, and a gap between the first and second brackets 44, 43 provided by the thin dielectric material 27 form a high impedance path, forcing currents to flow on the surface of the metallic sheet 64, containing seam 88 under test. A potential will be developed across a seam if the seam under test has a flaw, which can be detected by the electrodes 28 and 29 and detector 52, such as a spectrum analyzer or a network analyzer. The apparatus can be moved along the seam continuously for a given frequency to detect flaws along the seam by monitoring the detector output. To isolate the detector, a unity gain amplifier having high input impedance can be used if the input impedance of the detector is not much higher than that of the seam under test. Again note that elements 43, 44, 12, 13, 16, and 17 represent an extension of a coaxial cable. In other words, the apparatus functions as a coaxial cable when placed on a conducting sheet such as a shielded enclosure. The preferred embodiment uses a thin dielectric sheet 60 placed over the area being tested, or bottom portion of the apparatus, where the apparatus contacts the metallic surface, so that resistive contact between the apparatus and the metallic surface does not occur.

It should be noted that the present invention relies upon currents rather than radiated fields. With a radiated field, it is difficult to isolate the radiation occurring from the seam under test, i.e., radiation is received from other seams that leak, unshielded wires and electrodes of the detector. Also in a radiated, conventional technique, the path of the wires in the detector varies uncontrollably, so it is impossible to control the configuration. It should be noted that in the present invention, wires 16 and 17 are fixed and do not move. Springs 14 and 15 automatically provide proper positioning of the electrodes 28 and 29 visa vis the flaw or seam to be tested. A seam in incomplete shields can be measured more accurately with the present invention. By comparison, radiating devices of conventional techniques transmit through all openings and seams in the shield and the source of a given radiation flaw cannot be localized, except low frequency magnetic fields. In the present invention radiation is contained within the brackets of the invention so that measurements are more focused and accurate.

Figure 3:
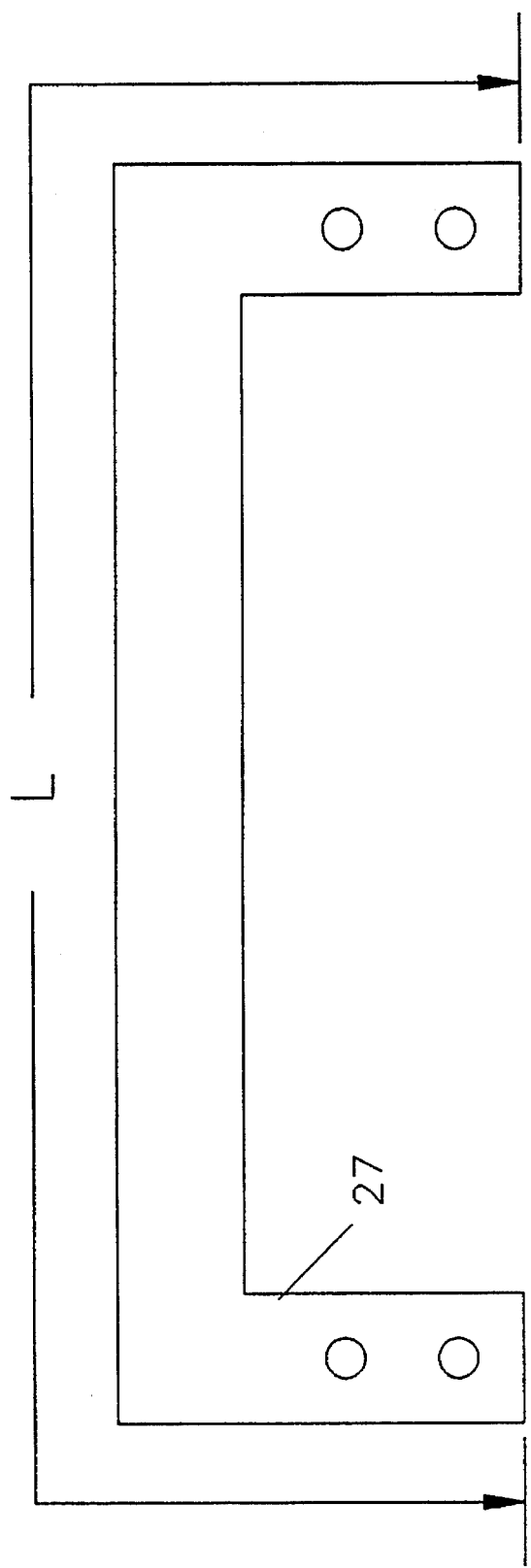
FIG. 3 illustrates the shape of the thin dielectric material placed at the center of the apparatus of the present invention.

As shown in FIG. 3, the operating frequency of the device is determined by the length L of the bracket, illustrated by the length of the thin dielectric material 27. The length L should be less than one-half the wavelength of the operating frequency to reduce radiation occurring through the gap provided by the thin dielectric material 27. Since the frequency is equal to 3 times $10^8$ divided by the wavelength, the length L of the device should be less than $3 \times 10^8$ divided by 2 times the frequency.

The radiation through the thin dielectric material 27 slot is small. Thus, the present invention does not measure radiation occurring from the device. The present invention measures only a voltage induced by currents flowing over the seam. The present invention can measure transfer seam impedance, after the device is calibrated, without exiting from one side of the enclosure.

The operating range of the present invention is from a few megahertz to tens of gigahertz in frequency. The present invention can be used to measure seams in situ on various surfaces such as flat, right angle, or bilevel. Seams can be checked during the construction phase of a shield room. The transfer seam impedance can be measured without exciting the seam from the opposite side of the shield. Thus, the present invention induces currents that flow through an area of the seam being checked and causes a voltage to develop across the seam if the seam has a flaw. The voltage developed across the seam can be measured using a voltage probe. The apparatus can be used in time domain using a transient pulse source, or in frequency domain, either single frequency or swept frequencies. The apparatus can also be used to measure quantitative transfer seam impedance by calibrating the device.

Figure 6:
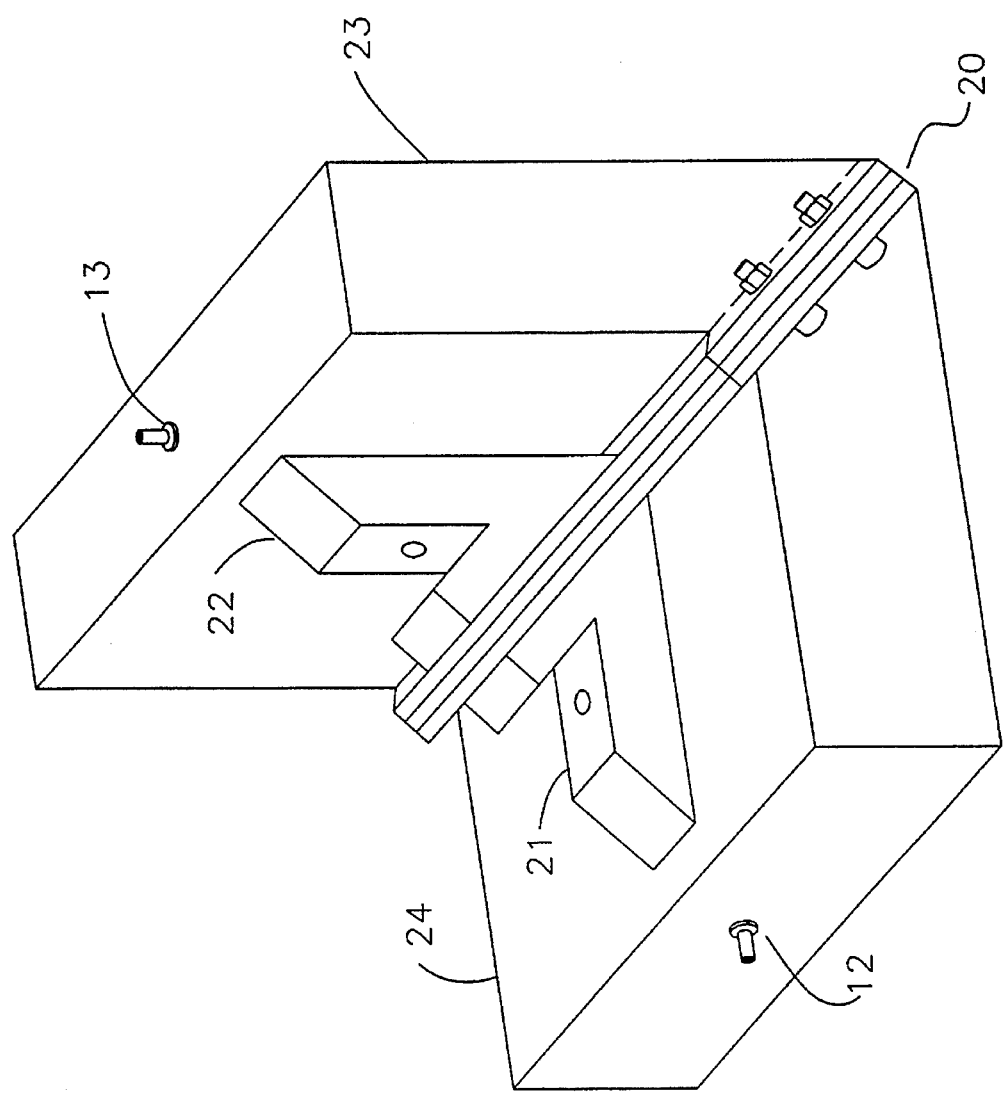
FIG. 6 illustrates a second embodiment of the present invention which is used on a seam located on a two-dimensional corner.
Figure 7:
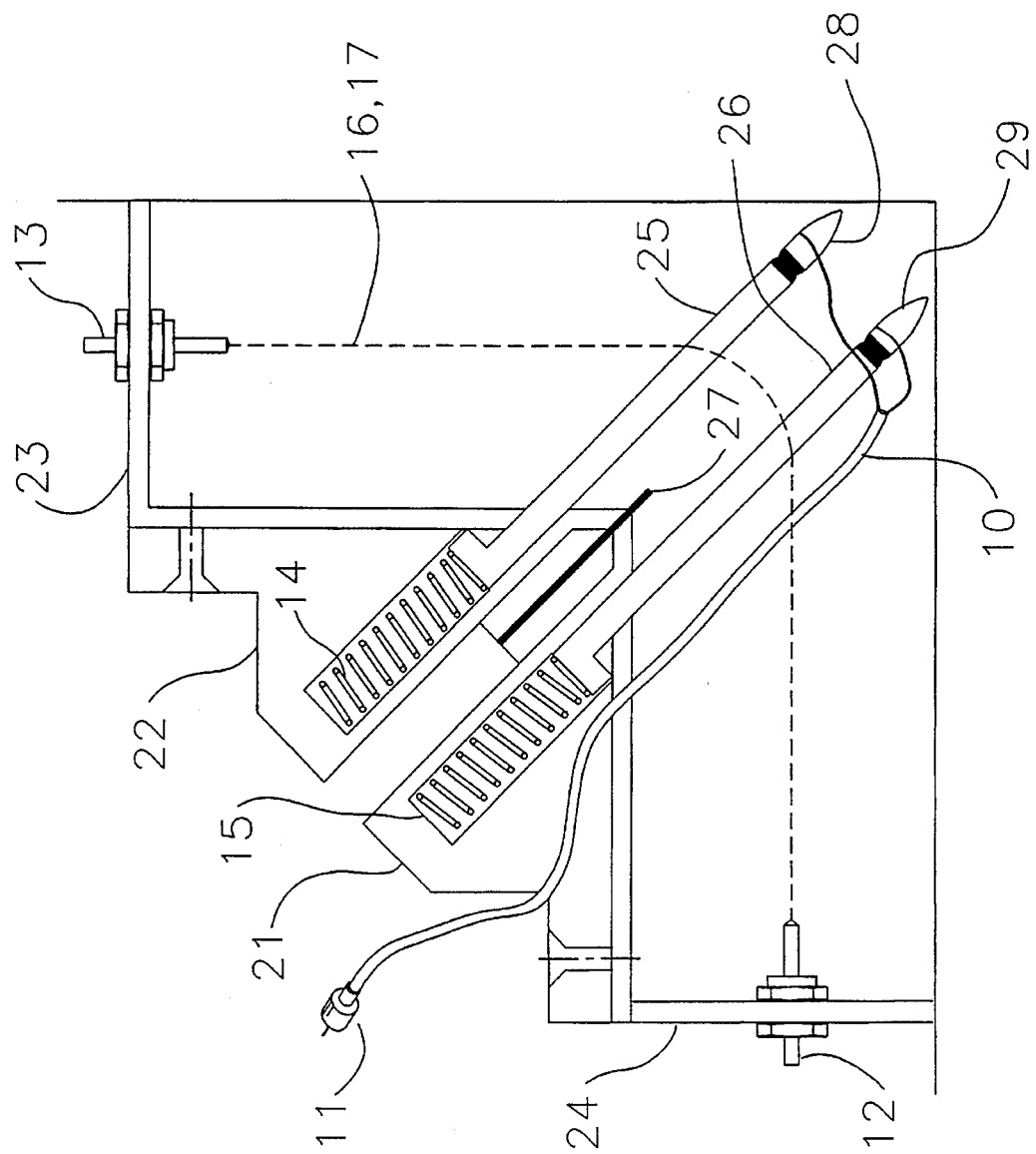
FIG. 7 is a center-cut side view of the second embodiment of the present invention.

FIGS. 6 and 7 illustrate a second embodiment of the invention. Brackets 23 and 24 are formed at 90-degree angle to permit easy measurement of a seam at a corner.

Figure 8:
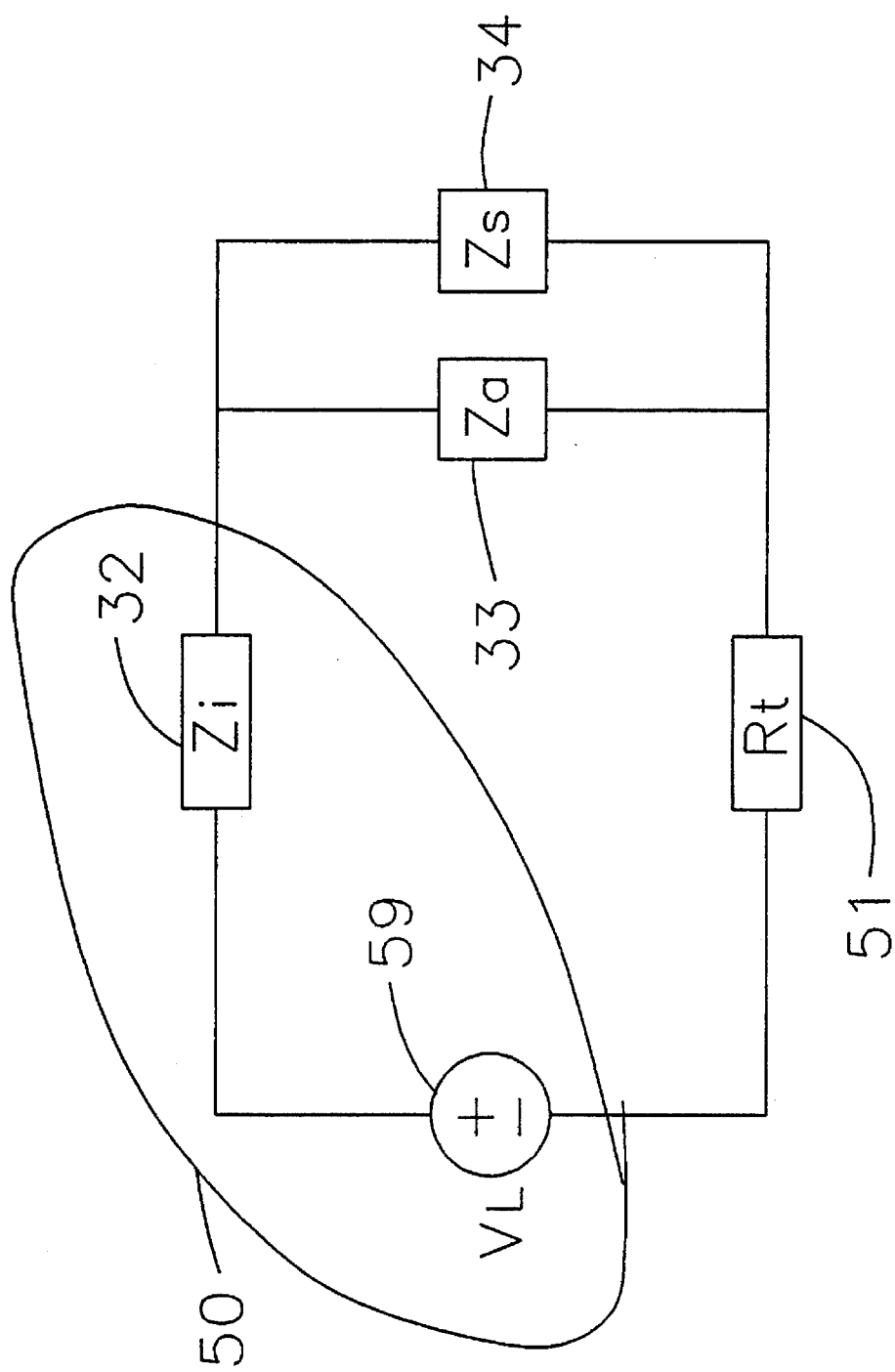
FIG. 8 is the equivalent circuit diagram of the apparatus of the present invention.

An equivalent lumped circuit diagram of the apparatus of the present invention when placed over a highly conducting sheet containing a seam is shown as FIG. 8. The signal source 50, includes a sinusoidal voltage source 59, and source impedance ($Z_i$) 32. Element 33 represents the equivalent impedance $Z_a$ provided by the apparatus of the present invention. $R_t$ is the termination resistance 51. In element 34, $Z_s$ represents the equivalent impedance of a seam and a portion of the conducting sheet enclosed by the apparatus. To excite a seam under test one needs to ensure that enough current will flow through a seam being tested ($Z_s$), and that can be accomplished by adjusting the capacitance, a predominate factor in $Z_a$, provided by the apparatus of the present invention. The capacitance can be adjusted by changing the thin dielectric material 27, using a different dielectric constant, and by changing the contact surface area between the extrusion and the dielectric material 27. Thus, it is easy to vary the impedance of the device of the present invention.

The apparatus of the present invention can be used well beyond one gigahertz in frequency, perhaps to tens of gigahertz. However, a miniature apparatus should be used for frequencies beyond one gigahertz.

As noted above, the apparatus of the present invention can be used in the time domain as well as frequency domain. To use the apparatus in the time domain, the input connector 12 should be connected to a time-varying current or voltage source, and a wide band detector should be connected to the output of the coaxial connector 11.

Those skilled in the art can recognize, or be able to ascertain, using no more than routine experimentation, many equivalents to the embodiments of the invention described herein.

These and all other equivalents are intended to be encompassed by the following claims.

I claim:

1. A method for detecting flaws in a seam of a shielded enclosure by forcing a current to flow over said shielded enclosure and said seam, comprising the steps of:
    a) placing a hollow metallic device, including a high impedance path and an opening, so that said opening encloses said seam, said device further including a first electrode and a second electrode,
    b) electrically coupling a continuous wave signal source to said device,
    c) resiliently pressing said first electrode and said second electrode toward said shielded enclosure so that said seam is positioned between said first electrode and said second electrode, and
    d) measuring a voltage across said seam between said first and second electrodes, to detect flaws in said seam, wherein said current through said seam is indicative of flaws in said seam.

2. The method of claim 1, wherein said high impedance path in said device forces current to flow over said shielded enclosure and across said seam.

3. The method of claim 2, wherein said high impedance path comprises a thin dielectric material with a high dielectric constant, said thin dielectric material is positioned in a gap in said hollow metallic device.

4. The method of claim 3, wherein said high impedance path further comprises a first metallic extrusion and a second metallic extrusion, said thin dielectric material is positioned between said first and second metallic extrusions.

5. The method of claim 3, wherein said thin dielectric material is positioned in parallel with said seam.

6. The method of claim 1, wherein said hollow metallic device is rectangular in shape.

7. The method of claim 1, wherein said first electrode is positioned at a first level and said second electrode is positioned at a second level which is different from said first level.

8. The method of claim 1, wherein said current flowing across said seam produces a voltage across said seam, said voltage is measured by a spectrum analyzer.

9. The method of claim 1, wherein a thin dielectric sheet is positioned between said hollow metallic device and said shielded enclosure.

10. The method of claim 1, wherein a transfer seam impedance is measured.

11. A hand held apparatus, for detecting flaws in a seam of a shielded enclosure by forcing a current to flow over said shielded enclosure and said seam, comprising:
    a) a hollow metallic device, including a high impedance path and an opening, positioned over said seam so that said opening encloses said seam,
    b) a first electrode and a second electrode which are mechanically coupled to said hollow metallic device,
    c) a first spring which resiliently presses said first electrode towards said shielded enclosure, and
    d) a second spring which resiliently presses said second electrode towards said shielded enclosure, wherein said seam is positioned between said first electrode and said second electrode, wherein said current flowing over said seam is indicative of flaws in said seam.

12. The apparatus of claim 11, wherein said high impedance path forces said current to flow over said shielded enclosure and across said seam.

13. The apparatus of claim 12, wherein said high impedance path comprises a thin dielectric material with a high dielectric constant, said thin dielectric material is positioned in a gap in said hollow metallic device.

14. The apparatus of claim 13, wherein said high impedance path further comprises a first metallic extrusion and a second metallic extrusion, said thin dielectric material is positioned between said first and second metallic extrusions.

15. The apparatus of claim 11, wherein said thin dielectric material is positioned in parallel with said seam.

16. The apparatus of claim 11, wherein said hollow metallic device is rectangular in shape.

17. The apparatus of claim 11, wherein said first electrode is positioned at a first level and said second electrode is positioned at a second level which is different from said first level.

18. The apparatus of claim 11, wherein a thin dielectric sheet is positioned between said hollow metallic device and said shielded enclosure.

19. A hand held apparatus, for detecting flaws in a seam of a shielded enclosure by forcing a current to flow over said shielded enclosure and said seam, comprising:

a) a first metal bracket including a first connector and a first extrusion, b) a second metal bracket including a second connector and a second extrusion, c) a thin dielectric material sandwiched between said first and second extrusions, so that said first and second brackets form a hollow metallic device with an opening, d) two insulated wires, each connecting said first connector and second connector, said two insulating wires forming an oval shape, e) a first electrode, mechanically coupled to said first metal bracket, and resiliently pressed towards said shielded enclosure, and f) a second electrode, mechanically coupled to said second metal bracket, and resiliently pressed towards said shielded enclosure, wherein said opening is positioned over said seam so that said seam is between said first electrode and said second electrode wherein said current over said seam is indicative of flaws in said seam.

20. The apparatus of claim 19, wherein said first and second connectors are coaxial connectors.

21. The apparatus of claim 20, wherein said second connector is electrically coupled to a continuous wave signal source.

22. The apparatus of claim 19, wherein said second connector is coupled to a termination resistor.

23. The apparatus of claim 19, wherein said high impedance path forces current to flow over said shielded enclosure and said seam.

24. The apparatus of claim 23, wherein said thin dielectric material is positioned in parallel with said seam.

25. The apparatus of claim 19, wherein said hollow metallic device is rectangular in shape.

26. The apparatus of claim 19, wherein said first and second metal brackets form a right angle for measuring corners.

* * * * *